United States Patent
Doguet et al.

(10) Patent No.: US 10,974,066 B2
(45) Date of Patent: Apr. 13, 2021

(54) IMPLANTABLE MEDICAL DEVICE COMPRISING AN OPTICAL UNIT

(71) Applicant: SYNERGIA MEDICAL, Mont-Saint-Guibert (BE)

(72) Inventors: Pascal Doguet, Mont-Saint-Guibert (BE); Benoit Olbrechts, Mont-Saint-Guibert (BE); Carmen Godfraind, Mont-Saint-Guibert (BE); Aurelie De Cock De Rameyen, Mont-Saint-Guibert (BE)

(73) Assignee: SYNERGIA MEDICAL, Mont-Saint-Guibert (BE)

( * ) Notice: Subject to any disclaimer, the term of this patent is extended or adjusted under 35 U.S.C. 154(b) by 59 days.

(21) Appl. No.: 16/326,983

(22) PCT Filed: Oct. 10, 2016

(86) PCT No.: PCT/EP2016/074134
§ 371 (c)(1),
(2) Date: Feb. 21, 2019

(87) PCT Pub. No.: WO2018/068807
PCT Pub. Date: Apr. 19, 2018

(65) Prior Publication Data
US 2019/0168022 A1    Jun. 6, 2019

(51) Int. Cl.
*A61N 1/36* (2006.01)
*A61N 1/375* (2006.01)
(Continued)

(52) U.S. Cl.
CPC ....... *A61N 5/0622* (2013.01); *A61N 1/36125* (2013.01); *A61N 1/36135* (2013.01);
(Continued)

(58) Field of Classification Search
CPC ...... A61N 5/06; A61N 5/0622; A61N 5/0601; A61N 2005/063; A61N 1/36; A61N 1/375;
(Continued)

(56) References Cited

U.S. PATENT DOCUMENTS

| 7,280,870 B2 | 10/2007 | Nurmikko et al. |
| 7,951,181 B2 | 5/2011 | Mahadevan-Jansen et al. |

(Continued)

FOREIGN PATENT DOCUMENTS

| WO | 2008036547 A1 | 3/2008 |
| WO | 2015164571 A2 | 10/2015 |

(Continued)

OTHER PUBLICATIONS

International Search Report dated Jan. 31, 2017 for International Application No. PCT/EP2016/074134 filed Oct. 10, 2016.

*Primary Examiner* — Carl H Layno
*Assistant Examiner* — Anh-Khoa N Dinh
(74) *Attorney, Agent, or Firm* — Blue Filament Law PLLC (57) ABSTRACT

An implantable medical device is detailed that includes a housing enclosing an electronic circuit and source of power, and an optical unit sealingly coupled to the housing, the optical unit including a monolithic block made of a transparent ceramic material and comprising: a thin window defined by an inner surface and an outer surface, an outer mating structure for coupling a fiber optic to the monolithic block, and an inner mating structure for permanently coupling a light unit, and a light unit rigidly mounted in the inner mating structure of the monolithic block. The light unit includes a light element including one or more of an inner light source, and/or a photodetector, the light element and a fiber optic engaged in the outer mating structure are in (Continued)

alignment with a corresponding reference point located on the thin window.

14 Claims, 7 Drawing Sheets

(51) Int. Cl.
*A61N 5/06* (2006.01)
*G02B 6/42* (2006.01)

(52) U.S. Cl.
CPC ......... *A61N 1/3754* (2013.01); *G02B 6/4204* (2013.01); *G02B 6/4228* (2013.01); *G02B 6/4246* (2013.01); *G02B 6/4248* (2013.01); *G02B 6/4251* (2013.01); *A61N 5/0601* (2013.01); *A61N 2005/063* (2013.01); *G02B 6/4292* (2013.01)

(58) Field of Classification Search
CPC .............. A61N 1/3754; A61N 1/36125; G02B 6/4251; G02B 6/4292; G02B 6/4246; G02B 6/4204
USPC .......... 607/80, 88, 93, 95; 600/178, 182, 191
See application file for complete search history.

(56) References Cited

U.S. PATENT DOCUMENTS

| 8,721,695 B2 | 5/2014 | Tass et al. |
| 2007/0253673 A1 | 11/2007 | Nielsen et al. |
| 2010/0114225 A1 | 5/2010 | Imran et al. |

FOREIGN PATENT DOCUMENTS

| WO | WO-2015164571 A2 * | 10/2015 | ........... A61N 5/0601 |
| WO | 2016131492 A1 | 8/2016 | |
| WO | 2017202455 A1 | 11/2017 | |

* cited by examiner

IMPLANTABLE MEDICAL DEVICE COMPRISING AN OPTICAL UNIT

TECHNICAL FIELD

The present invention concerns an implantable medical device (IMD) for use in a medical treatment involving the transmission of light through one or more fibre optics, either from or to the implantable medical device. The present invention enhances the longevity of the electronics contained inside the IMD's by reducing the number of joints, preferably down to a single joint, and thus preventing the ingress of moisture and body fluids, as well as protecting the body from pollutants contained within the sealed device. It also increases the efficacy of light transmission by an accurate alignment of the various components of the light transmission assembly to levels never obtained to date in the field of IMD's.

BACKGROUND OF THE INVENTION

Implantable medical devices (IMD) have been used for decades for treating a number of disorders, in particular heart and neurological disorders. One type of IMD's consists of neurostimulators, which deliver electrical pulses to a tissue such as a nerve, a muscle or brain tissue for diagnosing or treating a number of disorders such as Parkinson's disease, epilepsy, chronic pain, motor disorders, and many other applications. In its simplest form, a device for delivering such electrical pulses comprises an electrical pulse generator, stimulating electrodes and wires electrically coupling the electrodes to the electrical pulse generator. In many applications, the electrodes must be applied directly onto the tissue to be treated, requiring the use of an implantable device. It is clear that miniaturization of the IMD's is of paramount importance.

Rather than conducting electrical current from an IMD containing the electronics, control and power source, through electrical conductors to electrodes fixed to a target tissue, several applications have been developed using light to transfer energy from an IMD to the electrodes through fibre optics. An example is described in PCT/EP2015/053585. The light energy is transformed into electric current by photovoltaic cells, said current being delivered to electrodes for stimulating the tissue to be treated. In some applications, a tissue can be stimulated by directing a light beam directly on a target tissue as described e.g., in U.S. Pat. Nos. 8,721,695 and 7,951,181. In optical stimulation applications, no electrode and no photovoltaic cell is required, since the light transmitted from the light unit through the fibre optic is directed onto the tissue to be treated.

Light can also be used to transfer information. Information can be transferred from one electronic component to another, or can be used for monitoring physiological functions of a human or animal body and sensing of various physiological parameters. For example, changes in light scattering of a light beam aimed at a target tissue can be provoked by potential variations in the tissue which are indicative of structural events in said tissue.

Because IMD's must be miniaturized, only small sources of energy are used, limiting their autonomy. A rechargeable battery can be used, of course, but the frequency of recharging the batteries must be reduced for two reasons. First, the service life of a rechargeable battery depends on the number of charging operations, as the capacity of the battery decreases with each new charging. Once the battery capacity becomes too low, the IMD must be replaced by a new one. The longer the period between two recharging operations, the longer the service life of the battery. Second, recharging a battery generally blocks the host of the IMD and prevents him from most non-static activities during the time required for the charging process. An example of recharging device is described, e.g., in PCT/EP2016/061722. For both non-rechargeable and rechargeable batteries, it is clear that energy cannot be wasted and the transfer of light from an emitter to a receiver must be as energy-effective as possible.

Another issue with IMD's is their longevity. In order to avoid having to replace an implanted medical device, it is desired that the service life time of an IMD be as long as possible. One of the major causes of failures of IMD's is infiltration of alien pollutants—in particular moisture—through degraded joints. A major issue are feedthroughs, commonly used for conducting electrical current from the outside of an IMD to the inside thereof and reversed. As its name suggests, a feedthrough is a pin extending through a wall of an IMD, bringing in conductive communication the inside of the IMD with the outer environment. Several feedthroughs are generally required and forming joints which are tight enough over a long period of exposure to the aggressive environment of a human or animal body is a challenge. Without surprise, feedthroughs constitute weak points of IMD's which are responsible for many recorded failures.

Feedthroughs can be used also to carry light between the inside and the outside of an IMD. For example, U.S. Pat. No. 7,280,870 describes an IMD comprising a fibre optic for transporting light between an outer fibre optic coupled to the IMD and the inside of the IMD. Alternatively, a window transparent to the light wavelengths to be transmitted can be installed between an outer fibre optic and the interior of an IMD containing a source of light, a photodetector, or an inner fibre optic. The window protects the interior of the IMD containing sensitive electronic circuits from the aggressive surrounding environment of the host body. Such windows must, however, also be sealed to the housing of the IMD.

Figure 1:
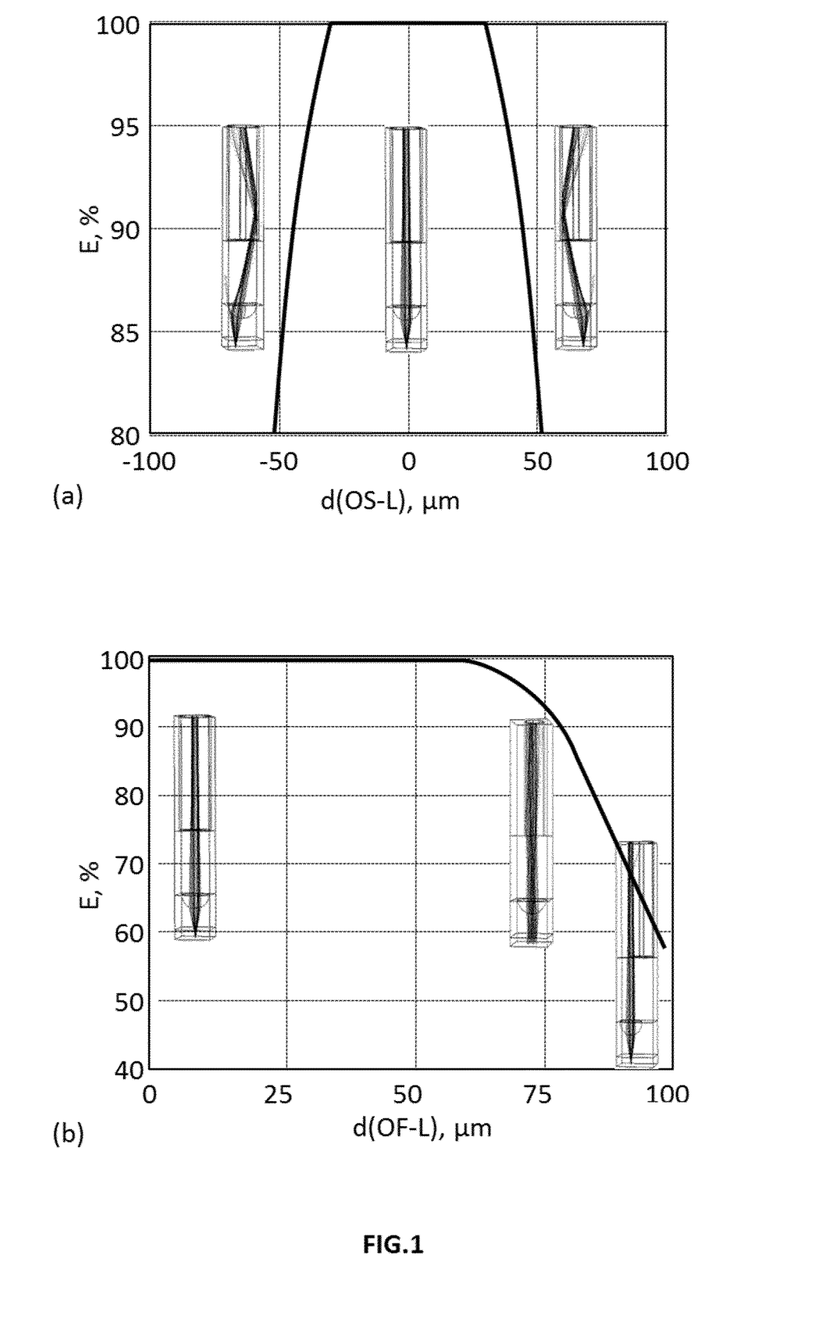
FIG. 1: shows the coupling efficiency, E (%), of light transmission between a source of light and an optical fibre as a function (a) of the misalignment, d(OS-L) between the light source and a micro-optics component provided at the inner surface of a thin window, and (b) of the misalignment, d(OF-L) between the fibre optic and said micro-optics component.

A light coupling unit between an outer fibre optic and the interior of an IMD is therefore generally composed of: (a) an outer fibre optic, (b) a coupling device for coupling the outer fibre optic to the IMD, (c) a window or inner fibre optic sealed to a wall of the IMD, (d) a source of light or photodetector located inside the IMD, (e) often a lens is located between the outer fibre optic and the source of light or photodetector to change the properties of the light beam, such as for example, converging the light beam onto a focal point. The efficacy of the transfer of light between the outer fibre optic and the source of light or photodetector is greatly dependent on the alignment between the various components of the light coupling unit. The alignment is rendered even more essential in case the window is provided with a lens modifying the properties of a light beam. FIG. 1 shows the coupling efficiency in % plotted as a function of (a) the misalignment of a source of light with a lens provided at an inner surface of the window of a coupling light unit and (b) the misalignment of said lens with an outer fibre optic. It can be seen that a misalignment of the order of 30-50 µm of either component with the lens yields a brutal drop of the light transfer efficacy between an outer fibre optic and the interior of an IMD. Considering that the IMD must be miniaturized, thus reducing the size of batteries, which limits the IMD's autonomy and that recharging batteries is a cumbersome operation, it is clear that the coupling efficacy between a fibre optic and the interior of an IMD must be optimized. This is only possible with an alignment of the various components of a light coupling unit of within less than 50 µm, preferably less than 30 µm.

Joining an element to a support structure by welding, allows the positioning of such element to be controlled to a precision of about 100-150 µm. Referring to the graphs of FIG. 1, it is clear that it is insufficient for ensuring an efficient transfer of light energy between an outer fibre optic and the interior of an IMD.

The present invention proposes an IMD comprising an optical unit wherein the various components are aligned within less than 30 µm, yielding a most efficient transfer of light energy between a fibre optic and the interior of the IMD. The number of joints can be substantially reduced compared with state of the art IMD's, down to a single outer joint in preferred embodiments. These and other advantages of the present invention are described more in details in the following sections.

SUMMARY OF THE INVENTION

The present invention is defined in the appended independent claims. Preferred embodiments are defined in the dependent claims. In particular, the present invention concerns an implantable medical device comprising:
(a) a housing (2) defining an inner volume separated from an outer environment, and enclosing an electronic circuit and source of power, and
(b) an optical unit (3) sealingly coupled to the housing, said optical unit consisting of:
a monolithic block unit (4) made of a transparent ceramic material which is transparent to wavelengths comprised between 300 and 2200 nm, and comprising:
a thin window (4w) defined by an inner surface facing the inner volume of the housing and an outer surface facing the outer environment,
an outer mating structure (4om) located on the side of the outer surface of the thin window, for coupling an outer fibre optic (9) in alignment with a corresponding reference point (4r) of the inner or outer surface of the thin window, and
an inner mating structure (4im) located on the side of the inner surface of the thin window, for permanently coupling a light unit (5), and
a light unit (5) comprising a light element including one or more of an inner light source (5L), and/or photodetector (5d), and/or inner fibre optic, said light unit being rigidly mounted in the inner mating structure (4im) of the monolithic block unit, such that one of the inner light source (5L), and/or photodetector (5d), and/or inner fibre optic is in alignment with said corresponding reference point (4r) of the inner or outer surface of the thin window.

As well known by a person of ordinary skill in the art, the term "transparent material" refers to materials having the physical property of allowing light to pass through the material without being scattered. On a macroscopic scale, the photons follow Snell's Law. A transparent material differs from a translucent material in that the latter allows light to pass through, but does not follow Snell's law on the macroscopic scale and the photons are scattered. Snell's law describes the relationship between the angles of incidence and refraction, when referring to light or other waves passing through a boundary between two different isotropic media, such as water, glass, or air. Snell's law states that, $\sin\theta_1/\sin\theta_2 = n_2/n_1$, wherein $\theta$ is the angle measured from the normal of the boundary, n is the refractive index, and the subscripts 1 and 2 refer to a first and second media of propagation of the light. Transparency is therefore an intrinsic property of a material and depends on the wavelength of the light and, for crystalline materials, it varies as a function of properties such as degree of crystallinity, size, number and orientation of crystal grains.

Transmittance of a light beam of a given wavelength by a material is the fraction of incident light beam power that is transmitted through the volume of a sample. Beside the intrinsic material properties such as transparency, transmittance therefore also depends on the geometry of the sample, in particular, the thickness, $\ell$, through which the light beam travels. By definition, the transmittance, T, decreases exponentially with the thickness, $\ell$, as, $T = e^{-\ell}$. Depending on the window material, windows having a high transmittance therefore may require a low thickness. In a preferred embodiment, the thin window of the monolithic block unit comprises a portion facing the light element having a thickness of not more than 2000 µm, preferably not more than 1000 µm, more preferably of not more than 500 µm. The transmittance of the optical portion is preferably at least 75%, more preferably at least 80% for wavelengths comprised between 300 and 2200 nm. The transparent ceramic material forming the monolithic block unit is preferably selected from: fused silica, borosilicate, spinel, sapphire, or yttrium oxide.

The implantable medical device of the present invention may comprise a micro-optics component for modifying the properties of a light beam which is either emitted by the inner light source in the direction of the outer surface, or emitted by an external light source in the direction of the inner surface and of the photodetector or inner fibre optic. The micro-optics component is preferably an integral part of the inner or outer surface of the thin window and/or is rigidly fixed to the light unit, preferably to the inner light source. It is preferred that the micro-optics component be an integral part of the thin window. In this embodiment, the corresponding reference point is preferably located on the micro-optics component which is integral to the inner or outer surface of the thin window.

In a preferred embodiment, the housing of an implantable medical device according to the present invention may be formed by at least a main housing element and a secondary element sealed to the main housing element by a secondary joint. The optical unit (3) can be an integral part of either the main housing element or the secondary element. Alternatively, the optical unit is sealingly coupled by a hermetic joint to an opening provided either in the main housing element or the secondary element. The hermetic joint and/or the secondary joint can be formed by brazing, by diffusion bonding, by eutectic bonding, by gluing (adhesive bonding), or by welding including metallization of the surfaces to be welded followed either by direct welding or by using intermediate metals including titanium or gold. In order to reduce the number of joints, it is preferred that the IMD of the present invention comprising no feedthrough. They are not essential to the functioning of the IMD, since energy can be transferred optically in and out of the housing through the thin window, and feedthrough joints are critical to the service life of an IMD.

In an implantable medical device according to the present invention, the light element is aligned with the corresponding reference point of the inner or outer surface of the thin window, with a tolerance of preferably less than 30 µm, more preferably less than 10 µm. A better alignment yields a longer autonomy of the IMD.

The present invention also concerns a kit-of-parts comprising:

(a) an implantable medical device as described supra, and
(b) a fibre optic comprising a proximal end provided with a connector mating the outer mating structure of the monolithic block, such that when connected to said outer mating structure, the fibre optic is in alignment with the corresponding reference point of the inner or outer surface of the thin window, with a tolerance of less than 50 µm, preferably less than 10 µm.

The proximal end of the fibre optic can be provided with a micro-optics component for modifying the properties of a light beam which is either emitted by the inner light source towards the fibre optic, or transmitted from the fibre optic towards the photodetector or inner fibre optic. The fibre optic comprises also a distal end, which is preferably provided either with,
(A) an electrodes unit, said electrodes unit comprising:
(a) a photovoltaic cell able to convert the light energy transported by the fibre optic into electrical current, and
(b) at least two electrodes electrically connected to the photovoltaic cell; or
(B) A micro-optics device for aiming an emitted light beam towards a target tissue The present invention also concerns an implantable medical assembly comprising:
(a) an implantable medical device as described above, and
(b) a fibre optic, comprising a proximal end provided with a connector mating and engaged in the outer mating structure of the monolithic block.

On the one hand, the fibre optic is in alignment with the corresponding reference point of the inner or outer surface of the thin window, with a tolerance of less than 50 µm, preferably less than 10 µm. On the other hand, the light element is in alignment with said corresponding reference point of the inner or outer surface of the thin window, with a tolerance of less than 30 µm, preferably less than 10 µm.

The present invention also concerns a process for producing an implantable medical assembly as described above comprising the following steps:
(a) providing a 3D computer assisted design of the monolithic block unit;
(b) providing a basic block of a transparent ceramic material, which is transparent to wavelengths comprised between 300 and 2200 nm, and of dimensions suitable for forming the monolithic block unit by removal of excess material;
(c) selectively treating with a laser the excess material to be removed from the basic block for forming the monolithic block unit such as to obtain a laser treated block, wherein the thus laser treated excess material is rendered more sensitive to an etching treatment,
(d) etching the laser treated block with a chemical composition such as to remove the laser treated excess material from the basic block and thus obtaining a monolithic block unit, and
(e) rigidly mounting to the inner mating structure of the monolithic block unit a light unit comprising a light element including one or more of an inner light source, and/or photodetector, or an inner fibre optic, such that the inner light source, or photodetector, or inner fibre optic be in alignment with the corresponding reference point of the inner or outer surface of the thin window, to form an optical unit.

In a preferred embodiment, the process further comprises the step of forming a housing (2) defining an inner volume separated from an outer environment, and enclosing an electronic circuit and source of power, such that the optical unit is sealingly coupled to the housing with the inner surface of the thin window facing the inner volume of the housing and the outer surface of the thin window facing the outer environment.

BRIEF DESCRIPTION OF THE FIGURES

For a fuller understanding of the nature of the present invention, reference is made to the following detailed description taken in conjunction with the accompanying drawings in which.

DETAILED DESCRIPTION OF THE INVENTION

Figure 2:
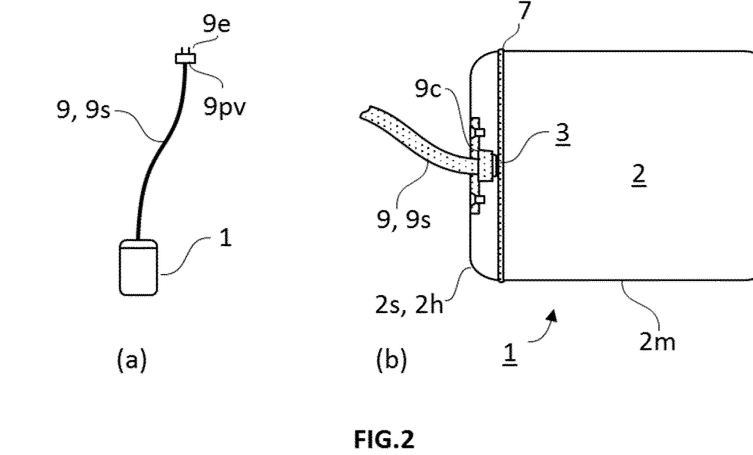
FIG. 2: shows (a) an implantable medical device according to the present invention coupled to a fibre optic provided with a photovoltaic cell and electrodes, and (b) an outer view of an assembly according to the present invention.

As illustrated in FIG. 2(a), an assembly according to the present invention comprises an implantable medical device (IMD) (1), coupled to a proximal end of a fibre optic (9) or of a bundle of fibre optics enclosed in a sheath (9s). In continuation, unless specifically otherwise indicated, the term "fibre optic" used in singular can also refer to a sheath (9s) enclosing a bundle of fibre optics. The fibre optic is provided at a distal end thereof with an element which, as illustrated in FIG. 2(a), can comprise electrodes (9e) connected to a photovoltaic cell (9pv) for converting the energy transmitted from a light source (5L) located inside the IMD through the fibre optic into electrical energy to be fed to the electrodes (9e). This kind of assembly is useful in particular for neurostimulators of the type described, e.g. in PCT/EP2015/053585.

Alternatively, a target tissue may be treated by aiming an emitted light beam at said target tissue. The distal end of the fibre optic must therefore be suitable for delivering said emitted light beam at a desired area of the target tissue, either concentrated into a small spot, or delivered over a soft spot, or even scattered over a large area of the tissue. To this purpose, the distal end of the fibre optic must have a specific geometry. The cross-section of the distal end can be planar or provided with a micro-optics device for aiming the emitted light beam towards a target tissue with the desired properties. Micro-optics devices may comprise a lens, a prism, a polarizer, a beam splitter, a mirror, a filter, and the like.

In yet an alternative application, a target tissue may be monitored by aiming an emitted light beam at said target tissue and by characterizing the properties variations of the light reflected by or transmitted through said target tissue. The distal end of the fibre optic can thus be provided with a sensor suitable for sensing variations in the properties of the reflected or transmitted light, which are representative of physiological changes in the target tissue. The sensor may send optical signals through the fibre optic to a photodetector (5d) located inside the IMD which may contain a processor for treating said optical signal. Alternatively, the photodetector (5d) in the IMD can be suitable for characterizing a property of the light reflected by or transmitted through the target tissue and conveyed to the IMD through the fibre optic, with no need of any sensor at the distal end of the fibre optic.

The gist of the present invention is in the IMD itself, in particular in the new concept of optical unit (3) illustrated in FIGS. 3 to 8. An IMD (1) according to the present invention comprises a housing (2) enclosing an electronic circuit and a source of power and any other elements used in IMD's including antennas, coils, etc. The housing defines an inner volume hermetically separated from an outer environment. The IMD further comprises an optical unit (3) sealingly coupled to the housing. The optical unit (3) consists of a monolithic block (4) made of a transparent ceramic material, and of a light unit (5) rigidly coupled to the monolithic block.

As illustrated in FIGS. 3 to 7, the monolithic block (4) comprises:
(a) a thin window (4w) defined by an inner surface facing the inner volume of the housing and an outer surface facing the outer environment;
(b) an outer mating structure (4om) located on the side of the outer surface of the thin window, for coupling a fibre optic (9) in alignment with a corresponding reference point (4r) of the inner or outer surface of the thin window, and
(c) an inner mating structure (4im) located on the side of the inner surface of the thin window, for permanently coupling the light unit (5).

Contrary to state of the art IMD's, the thin window (4w) is an integral part of the monolithic block and is not a separate window assembled to a header by an additional joint. This has two major advantages over prior art constructions. First, it reduces the number of joints, which are expensive to form and have a limited service life, identified as a major cause of IMD's failures. Second, the position of the thin window can be controlled to within less than 50 μm, preferably less than 30 μm, more preferably less than 20 μm. This is particularly critical in case micro-optics components are provided on the inner or outer surface of the thin window, because as shown in FIG. 1, a misalignment of the light source or the outer fibre optic of less than 50 μm yields substantial losses of efficacy in the transfer of optical energy.

The outer mating structure (4om) is also an integral part of the monolithic block and can therefore be formed in quasi-perfect alignment with the thin window, as they are both integral with the monolithic block. A tolerance of alignment between the outer mating structure and the thin window is such that a fibre optic (9) engaged in the outer mating structure can be in alignment with the corresponding reference point (4r) on the inner or outer surface of the thin window within less than 50 μm, preferably less than 10 μm.

Figure 8:
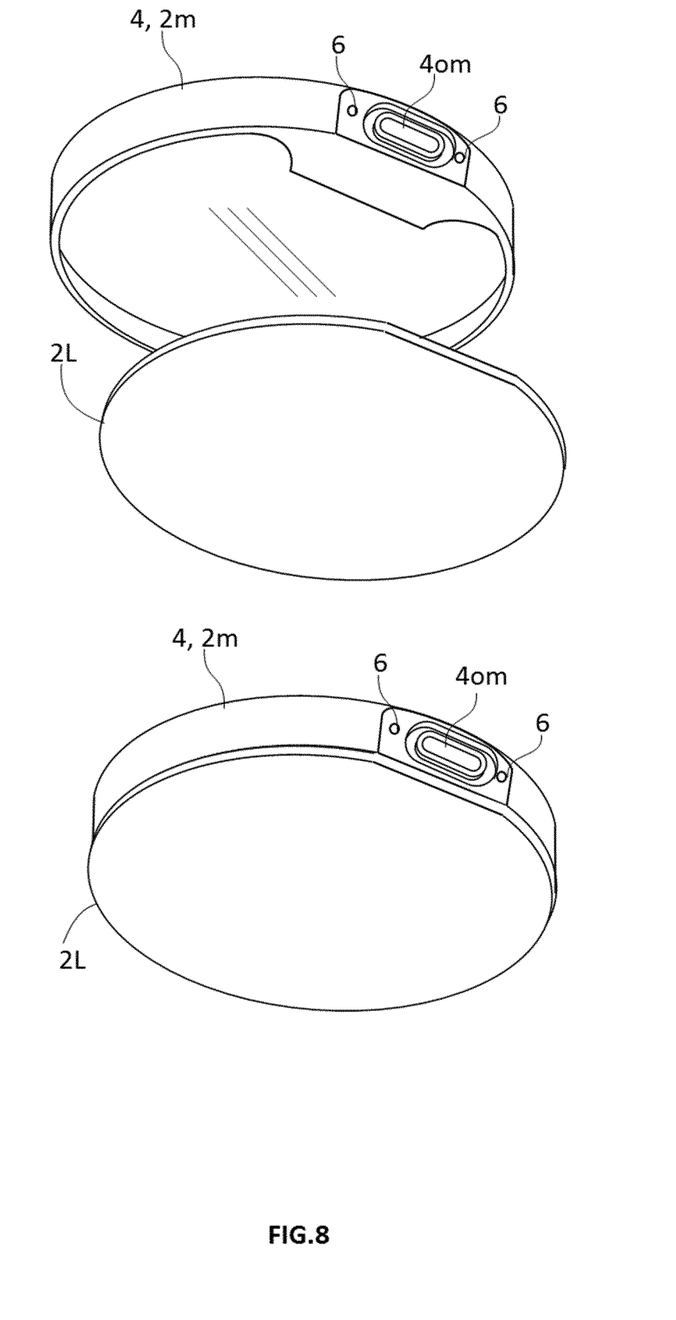
FIG. 8: shows views of yet an alternative optical unit according to the present invention.

In order to allow the loading of all the components to be housed within the inner volume defined by the housing, the housing is generally composed of at least a main housing element (2m), which defines a cavity which will form the inner volume of the housing when sealed by a secondary element (2s) to be sealingly coupled to the main housing element by a secondary joint (7s). For example the secondary element (2s) can be a header (2h) as illustrated in FIGS. 3 to 6, or a lid (2L) as illustrated in FIG. 8. A header (2h) differs from a simple lid (2L), in that beside sealing an opening, a header acts as an electrical and/or optical interface between the inner volume of the housing and the outer environment, by being equipped with a number of electrical feedthroughs and/or optical units. The header can be capped on the outer side with an epoxy coating for stabilizing the feedthroughs or for embedding an antenna. Like a lid, the header must be impervious to gases and liquids.

Figure 3:
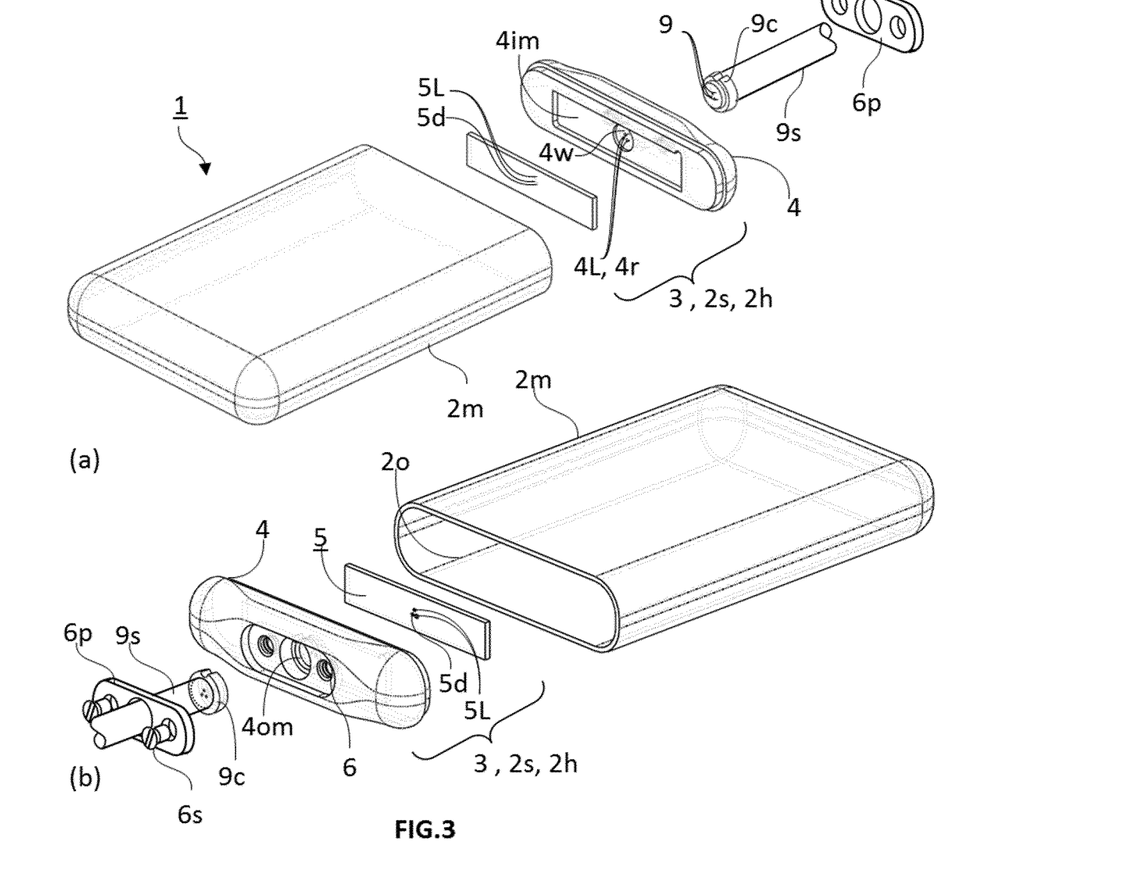
FIG. 3: shows exploded views of the elements of a kit-of-parts according to the present invention.
Figure 4:
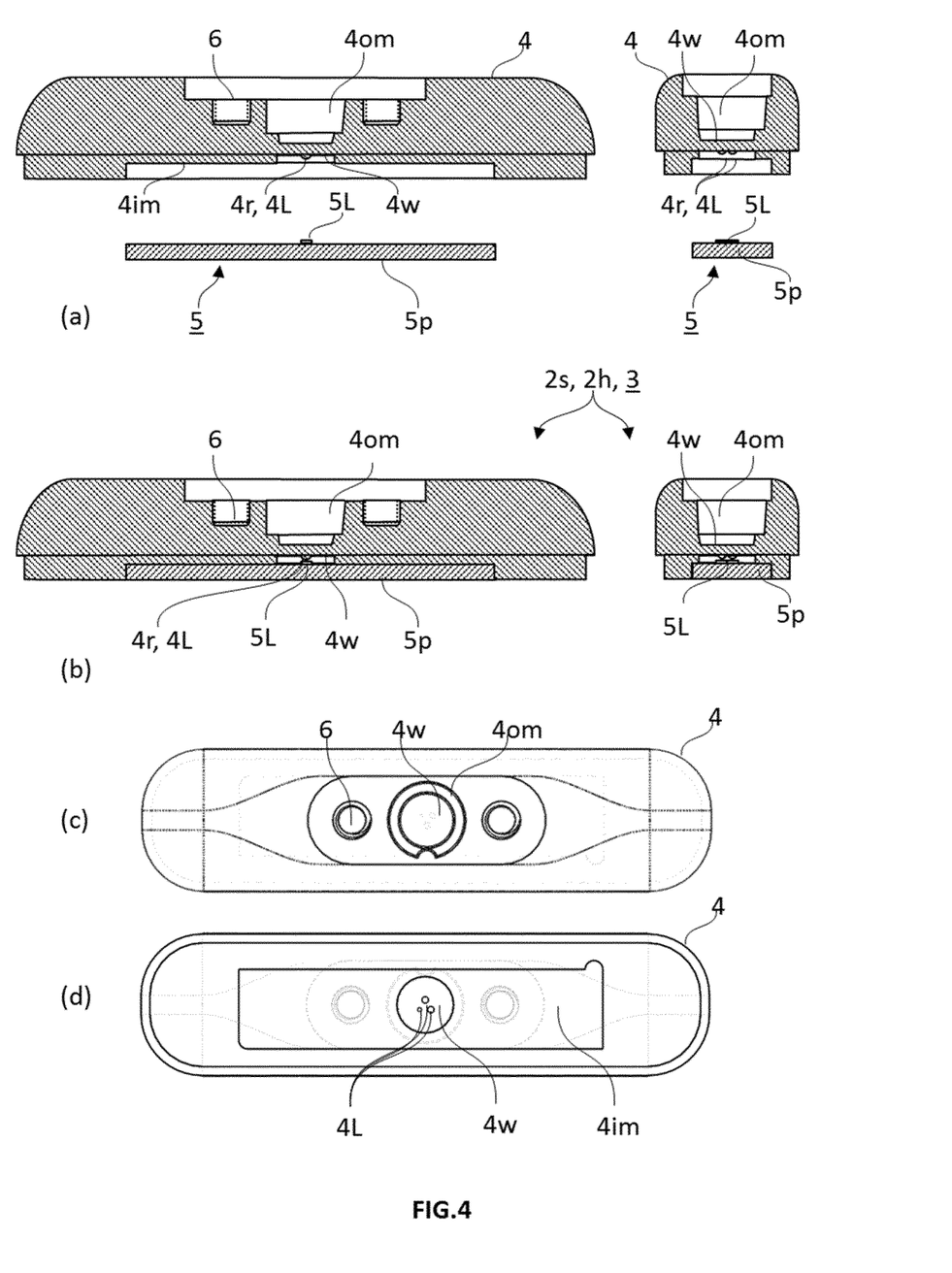
FIG. 4: shows views of an optical unit according to the present invention.
Figure 5:
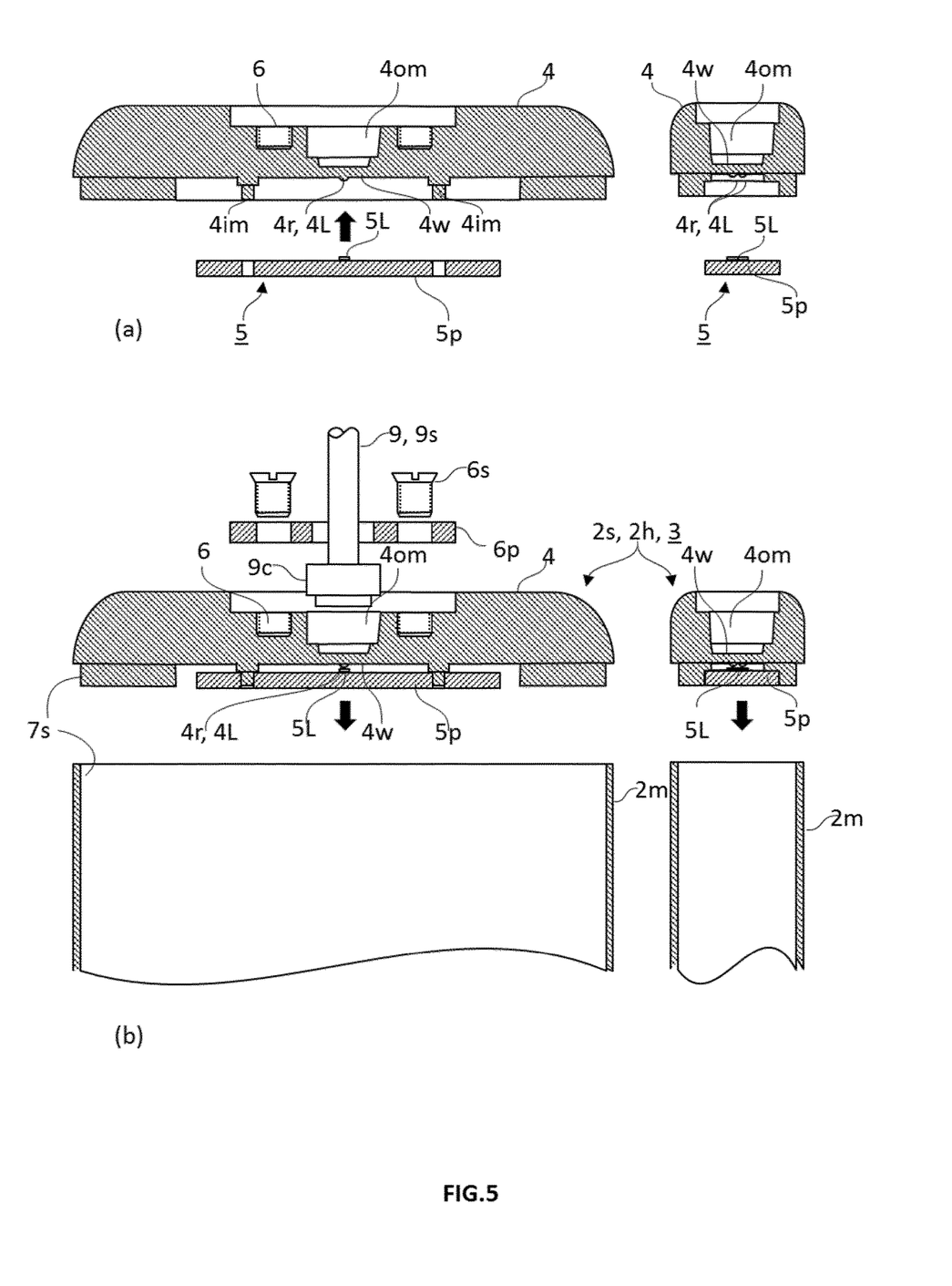
FIG. 5: shows views of an alternative optical unit according to the present invention.
Figure 6:
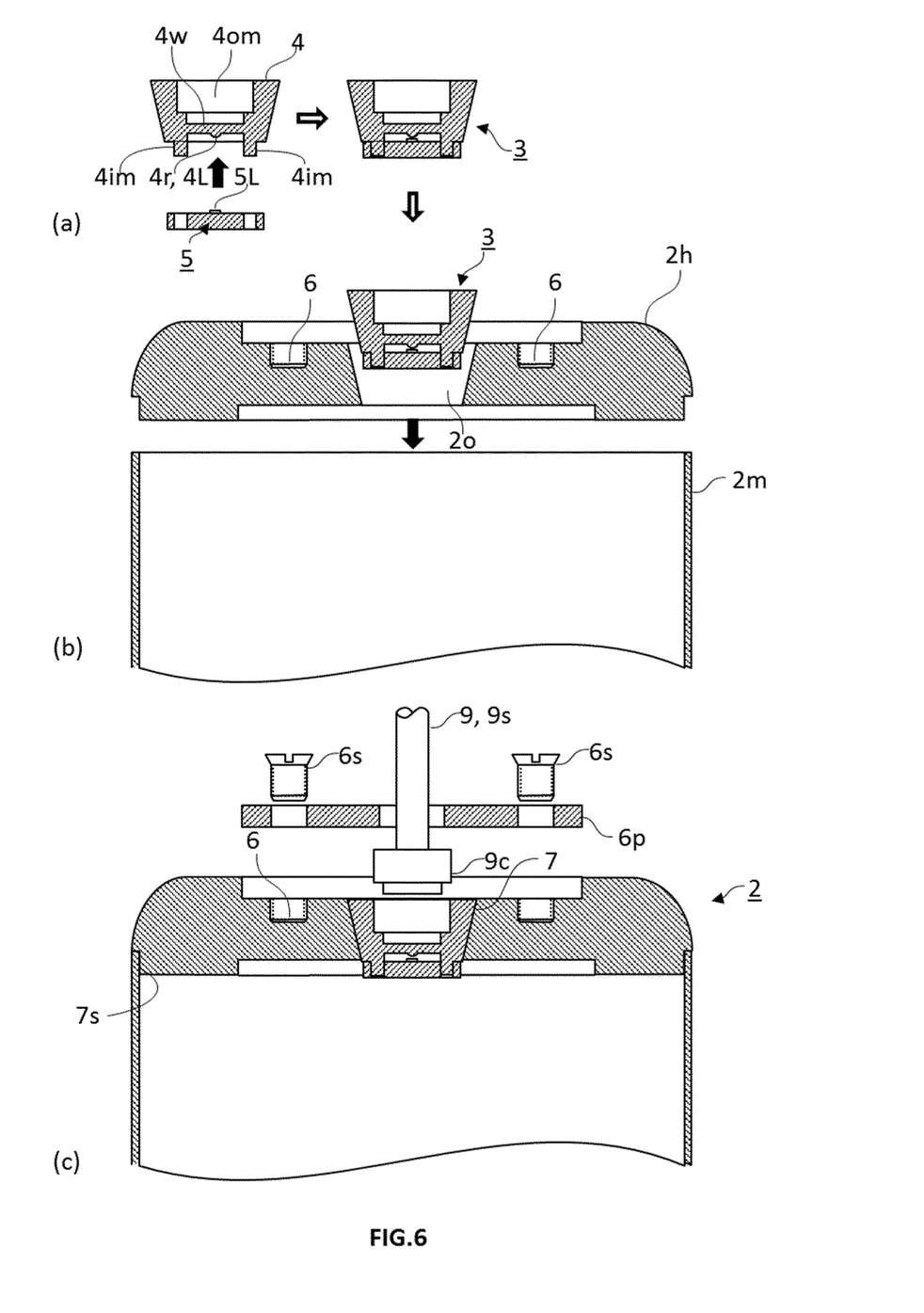
FIG. 6: shows views of yet an alternative optical unit according to the present invention.

In a first embodiment, the optical unit (3) can be an integral part of the main housing element (2m) or of the secondary element (2s). For example, FIGS. 3 to 5 illustrate an embodiment wherein the optical unit (3) forms a header (2h) of the housing. Additionally to forming part of the optical unit (3) and to supporting the light unit (5), the monolithic block unit (4) is shaped to form a header fitting an opening (20) provided in the main housing component, and sealed thereto by a secondary joint (7s). In this embodiment, the secondary joint (7s) between the header and the main housing element can advantageously be the sole external joint separating the inner volume from the outer environment. It is preferred that the IMD comprises as single external joint a secondary joint (7s). This is advantageous in that the probability of a leak is reduced. An external joint in the housing is any joint between two elements exposed to both housing inner volume and outer environment. It is advantageous to have a single external joint, because the secondary joint is of large dimensions and easy to form, unlike joints around feedthroughs required in state of the art IMD's, which are much smaller in dimensions and more complex to form with little room for handling due to the presence of generally several feedthroughs in a small area. It is clear that, instead of being an integral part of a header, the optical unit can be an integral part of a lid.

In another example illustrated in FIG. 8, the optical unit (3) can be an integral part of the main housing element (2m). The main housing element thus forms the monolithic block unit, forming part of the optical unit, supporting the light unit, and defining a cavity for receiving all the components to be contained within the inner volume of the IMD. The secondary element (2s) could be a lid (2L) sealing the inner volume from the outer environment by means of a secondary joint. Here again, the secondary joint is advantageously the sole external joint of the IMD.

In a second embodiment, the optical unit (3) can be sealingly coupled by a hermetic joint (7) to an opening (20) provided in the housing. In one example illustrated in FIG. 6, the optical unit is sealingly coupled to an opening provided in a secondary element (2s) forming a header (2h), by means of a hermetic joint (7). Unlike the monolithic block unit (4), the header (2h) in this embodiment needs not be transparent. The header is sealed to the main housing element by means of a secondary joint (7s).

Figure 7:
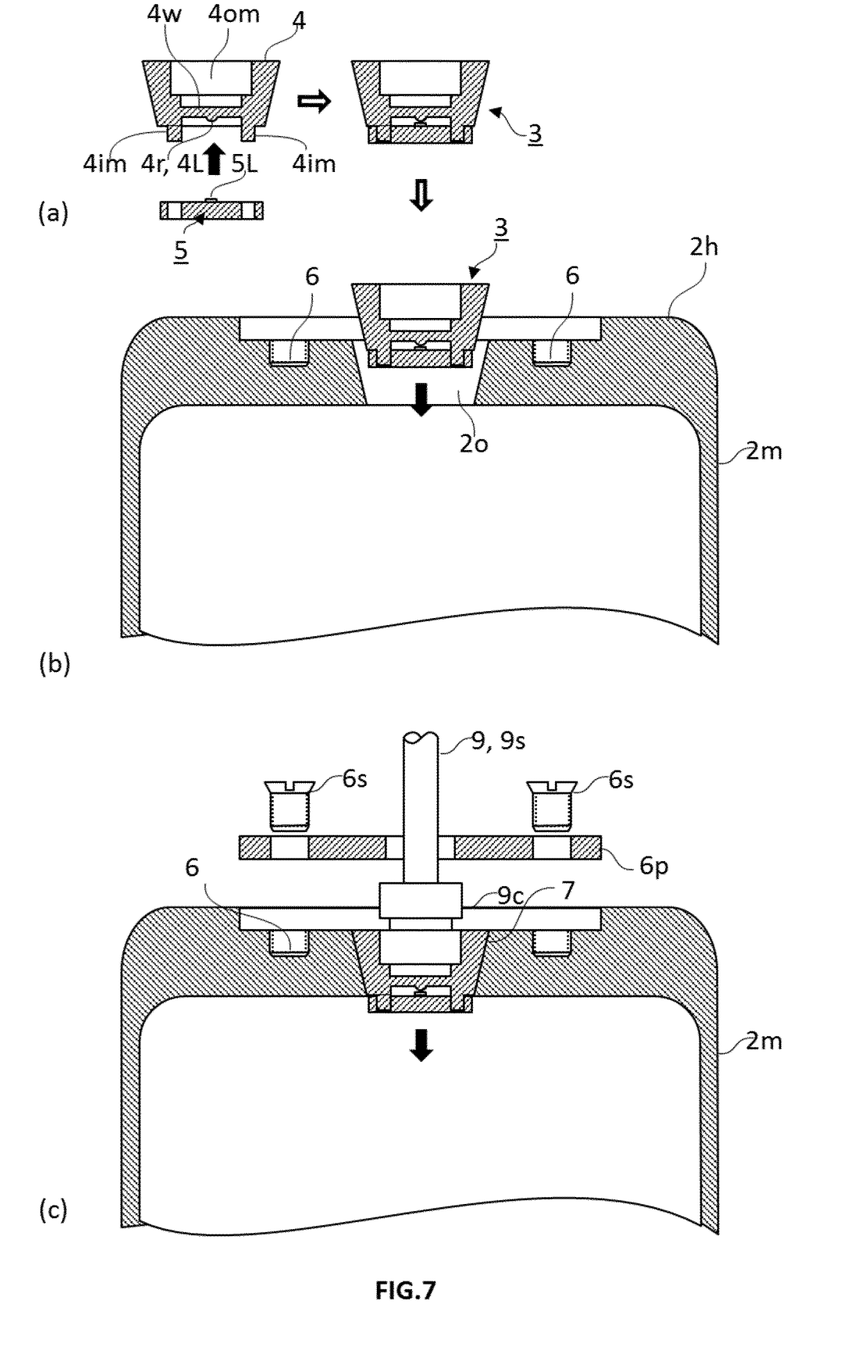
FIG. 7: shows views of yet an alternative optical unit according to the present invention.

In yet another example illustrated in FIG. 7, the optical unit (3) can be sealingly coupled to an opening (20) provided in the main housing element (2m) by means of a hermetic joint (7). Again, the main housing element needs not be transparent. The secondary element (2s) can be a header (2h) or a lid (2L) and can be sealingly coupled to the main housing element by means of a secondary joint (7s).

In the first embodiment wherein the optical unit (3) is an integral part of either the header, or the main housing element of the IMD's housing, it is preferred that the optical unit (3) also comprises fixing means (6) for fixing to the monolithic block a fibre optic engaged in the outer mating structure. For example, as illustrated in FIGS. 3 and 5 to 7, the fixing means can comprise threaded cavities for receiving screws (6s). A plate (6p) can be screwed to the fixing means for securing the connector (9c) in place. Other fixing means can be used which are discussed below.

Regardless of whether or not the optical unit is an integral part of an element of the IMD's housing, it is most preferred that an IMD according to the present invention comprises no feedthrough. In all cases, an IMD can comprise more than one optical unit. This could be used for example for the neurological treatment of Parkinson's disease, which requires stimulations in both right and left brain hemispheres with two pairs of electrodes. For such applications, it is also possible to use an IMD comprising an optical unit (3) made of a single monolithic block unit (4) and more than one light units (5).

The light unit comprises a light element including one or more of an inner light source (5L), and/or a photodetector (5d), and/or an inner fibre optic. FIG. 3 illustrates as an example, a light unit comprising two inner light sources (5L) and one photodetector (5d) mounted on a printed circuit board (5p). The thin window (4w) comprises three micro-optics components, each in alignment with a corresponding inner light source (5L) and photodetector (5d). The centre points of the micro-optics components form the corresponding reference points (4r) for each of the corresponding inner light sources (5L) and photodetector (5d). With such configuration, it is clear that three separate fibre optics (9) are required, which proximal ends must be in alignment with a corresponding reference point (4r) as discussed supra and a corresponding inner light source (5L) and photodetector (5d). The three fibre optics (9) are preferably bundled in a sheath (9s) which gathers and protects them from the external environment. FIG. 3 illustrates an embodiment comprising two inner light sources (5L), one photodetector (5d), three micro-optics components (4L) forming three corresponding reference points (4r), and three fibre optics (9). It is clear that the numbers, N, of components can be varied, as long as there is a same number, N, of fibre optics (9), reference points (4r), and total number, N, of inner light sources (5L), and/or photodetectors (5d), and/or inner fibre optics. In one embodiment, N=1. In the embodiment illustrated in FIG. 3, N=3. In an alternative embodiment, N=2, preferably comprising one inner light source and one photodetector (5d). N can take any integer value, depending on the applications and limited only by the space available in the optical unit.

An inner fibre optic or other waveguide (e.g., a prism) in alignment with the corresponding reference point (4r) (not shown) can be used to lead a light beam from an inner light source towards the thin window or from the thin window towards a photodetector, wherein the inner light source or photodetector is not in alignment with the corresponding reference point (4r). The principle remains the same, as the alignment of the different components: fibre optic (9), thin window (4w), micro-optics component (4L), and inner fibre optic must be as perfect as possible, within a tolerance of less than 50 µm, preferably less than 30 µm, more preferably less than 20 µm.

The inner light source (5L) and/or photodetector (5d) are preferably electronic components mounted on a printed circuit board (PCB). In particular, the light source is preferably a LED or a VCSEL. The peripheral geometry of the PCB, as well as the position of the inner light source or photodetector within the PCB can be controlled very accurately. Advantageously, the board of the PCB is made of ceramic, such as aluminium nitride, and can be laser cut with an accuracy of the order of the µm. Another advantage of a ceramic PCB is the similarities of coefficients of thermal expansion (CTE) with the ceramic material of the monolithic block unit. The PCB can then be coupled to the inner mating structure (4im) of the monolithic block unit such that the inner light source or photodetector is aligned with the corresponding reference point (4r) of the inner or outer surface of the thin window. As illustrated in FIG. 1(a), the tolerance in the alignment should be less than 30 µm, preferably less than 10 µm, in order to ensure a high efficacy of optical energy transfer. FIGS. 3(a), 4(a), and 4(d) show an inner mating structure (4im) in the shape of a recess in the monolithic block, having a perimeter slightly larger than the perimeter of the PCB holding the inner light source and photodetector. By positioning the PCB within the recess and forcing it against a reference corner of the recess, an optimal alignment of the inner light source or photodetector with the corresponding reference point can be achieved.

Other geometries of the inner mating structure can be used instead. For example, as illustrated in FIG. 5, the inner mating structure (4im) can be formed by a number of pins (integral to the monolithic block) suitable for receiving a PCB provided with a corresponding number of holes, snugly fitting into the pins. The pins may comprise a shoulder of diameter larger than the holes in the PCB, for controlling the distance of the PCB from the inner surface of the thin window.

The material forming the monolithic block must be impervious to the fluids and gases present inside a host body, as well as to any pollutant contained inside the housing of the IMD. Polymers such as silicones, epoxies, or fluorocarbons are ineffective because their permeability is too high for ensuring an effective long term protection (years) of electronics contained inside the IMD. Practically, only ceramics (both glasses and crystalline) and metals have a sufficiently low permeability for use in IMD's components separating the inside from the outside of said IMD's. Liquid crystal polymers are currently being developed with promising values of permeability. Because the thin window must be transparent to light beams and is an integral part of the monolithic block unit, the latter must necessarily be made of a material transparent to light beams. Practically all metals are opaque to light, whilst several ceramic materials, both crystalline and amorphous (=glasses), are transparent to light. The monolithic block unit used in the present invention is therefore made of a transparent ceramic material. In case liquid crystal polymers become available with a sufficiently low value of permeability, they could possibly be considered in the present invention in place of the transparent ceramic material.

The transparent ceramic material forming the monolithic block unit must be transparent to wavelengths comprised between 300 and 2200 nm, which are the wavelengths traditionally used for sending optical energy to a photovoltaic cell (9pv) for feeding electrodes (9e) with electrical current pulses, as well as for receiving information from the body by sensors. The transparent ceramic material can be selected for example from: fused silica, borosilicate, spinel, sapphire, or yttrium oxide.

The thin window is a critical part of the optical unit. It must allow the passage of light therethrough with a minimum of energy absorption. The thin window (4w) preferably comprises an optical portion facing the light element, and having a thickness of not more than 2000 µm, preferably nor more than 1500 µm, more preferably not more than 1000 µm, more preferably of not more than 500 µm. The thickness of said optical portion preferably ensures a transmittance of said optical portion of 75%, preferably at least at least 80% for wavelengths comprised between 300 and 2200 nm. The optical portion of the window can be defined by parallel inner surface and outer surface, which can be planar or curve. Alternatively, the optical portion may comprise a micro-optics component (4L), such as a lens which can be convex or concave.

The main housing element (2m) and the secondary element (2s) are sealingly coupled to one another by means of a secondary joint (7s). In some embodiments discussed supra, the optical unit (3) can be coupled to an opening (2o) of the housing by means of a hermetic joint (7) (cf. FIG. 2(b)). As discussed supra, the optical unit preferably forms an integral part of the main housing element or of the secondary element, and generally includes fixing means for fixing the fibre optic (9) to the optical unit. This embodiment is preferred because, a single external joint (=the secondary joint (7s)) is sufficient for sealing the inner volume of the IMD from the outer environment. The secondary joint (7s) and the hermetic joint (7) between the optical unit and the housing can be formed by any one of brazing, diffusion bonding, eutectic bonding, gluing (adhesive bonding, e.g., with a ceramic cement), or welding including metallization of the surfaces to be welded followed either by direct welding or by using intermediate metals including titanium or gold, such as by laser welding. These techniques are known to persons of ordinary skill in the art and ensure a tight and hermetic joint (7).

The secondary joint (7s) and; in case the housing comprises more than one joint (e.g., a hermetic joint (7)), all the joints of the housing must be hermetic according to standards specific to the application. For example, in the field of cochlear implants, the norm EN45502-2-3 applies and defines in § 19.6 that: "The implantable STIMULATOR case of an IMPLANT SYSTEM intended in normal use to be in contact with body fluids shall provide sufficient hermeticity so that no fluid can infiltrate the STIMULATOR case." Hermeticity can be tested for fine and gross leaks in accordance with EN 13185 and EN 1593. Compliance with the standard EN45502-2-3 shall be confirmed if the device leak rate does not exceed $5 \cdot 10^{-9}$ Pa m$^3$/s for fine leaks and if no definite stream of bubbles can be detected.

The foregoing joining techniques may yield the required hermeticity but they do not afford the tolerance of less than 50 µm, preferably less than 30 µm, required for an efficient transfer of light energy between inside and outside an IMD, which has been a recurrent problem in state of the art IMD's using light as source of energy or information. In the present invention, the positioning accuracy afforded by the hermetic joint is irrelevant for the alignment of the different optical components forming the optical unit (as long as the joint is indeed hermetic). Indeed, since all the components of the optical unit (3) including: light source (5L) or photodetector (5d), thin window (4w), micro-optics component (4L), and fibre optic (9), are all well aligned in the optical unit, the alignment of the optical unit itself with respect to the housing is not an issue anymore, and traditional joining techniques can be used in spite of their lack of positioning accuracy.

A fibre optic (9) can preferably be coupled in situ to the optical unit of the IMD because the location of the tissue to be treated is generally distant from the position of the implanted medical device. The fibre optic can be positioned into the body by running it under the skin without having to open the body over the whole length of the fibre optic. It is generally positioned separately from the IMD, to which it must then be connected. It is therefore advantageous to provide the fibre optic with a connector suitable for being easily connected in situ by a surgeon to the IMD with a high level of accuracy. The connection must be accurate and preferably reversible, so that an IMD can be replaced by a new one without having to remove the fibre optic. According to the present invention, the fibre optic therefore comprises a proximal end provided with a connector (9c) mating the outer mating structure (4om) of the monolithic block unit. When the connector is inserted by a surgeon into the outer mating structure, the fibre optic is in alignment with the corresponding reference point (4r) of the inner or outer surface of the thin window, with a tolerance of less than 50 µm, preferably less than 10 µm. Such tolerances cannot be achieved with traditional IMD's, because the position of a window assembled to a header and, hence, of the corresponding reference point, cannot be controlled with sufficient accuracy. Fixing means (6) can further be provided for fastening the thus inserted connector to the IMD. The fixing means (6) can comprise screws, bayonets, rivets, snap fittings, glue, welding, etc. Reversible fixing means are preferred for the reasons discussed supra, including screws, bayonets, and snap fittings. FIGS. 3 and 5 to 7 illustrate fixing means (6) consisting of screws fitting corresponding threads, for fixing a washer to the header of the IMD and thus fastening the fibre optic. The fixing means do not contribute to the alignment of the fibre optic with respect to the corresponding reference point, but simply stabilize the fibre optic in its aligned position, ensured by the outer mating structure.

Micro-optics components are advantageously positioned between the fibre optic proximal end and the light unit (5), when the optical properties of the light beam need to be modified. A micro-optics component can be one of a lens, for example, a converging lens for focusing the light beam onto a focal point; a prism for deviating the beam, a fan-out grating for scattering the light beam, a polarizer, a beam splitter, a mirror, a filter, and the like. The relative alignment of such micro-optics component and the other elements of the optical unit (3) is most critical. Micro-optics components have typical diameters of the order of 200-400 µm, and can form a protrusion of height, or a recess of depth comprised between 1 and 100 µm, preferably between 5 and 50 µm. If a light beam is not well aligned with the micro-optics component, a substantial loss of efficacy is observed (cf. FIG. 1). In order to ensure the best possible alignment of a micro-optics component (4L) with the light source or detectors and with the optical fibre, one of the following configurations is preferred:
  (a) the micro-optics component (4L) is an integral part of the inner or outer surface of the thin window (4w); or
  (b) the micro-optics component (4L) is rigidly fixed to the light unit (5L), preferably to the inner light source (5L), photodetector (5d), or inner optical fibre; or
  (c) the micro-optics component (4L) is rigidly fixed to the proximal end of the fibre optic (9).

Any of these configurations allows an accurate positioning of a micro-optics component within the optical unit and fibre optic. It is preferred that the micro-optics component (4L) be an integral part of the inner or outer surface of the thin window (4w) as illustrated in FIGS. 3 to 5.

The fibre optic comprises a distal end, opposite the proximal end. In some applications, a tissue may be treated by exposure to a light beam. In this case the distal end of the fibre optic can simply comprise means for fixing said distal end in a position suitable for irradiating said light beam onto a target tissue. The distal end may also be provided with a micro-optics device which can be selected among the same components as discussed with respect to the micro-optics component (4L) discussed supra. As illustrated in FIG. 2(a), the distal end of a fibre optics of a neurostimulator can be provided with an electrode unit comprising:
- (b) a photovoltaic cell (9pv) able to convert the light energy transported by the fibre optic into electrical current, and
- (c) at least two electrodes (9e) electrically connected to the photovoltaic cell.

In a neurostimulator, the electrodes can be coupled to a tissue of the host patient, such as a nerve or a muscle, for sending electrical pulses and thus stimulating the tissue. Alternatively, the distal end of the fibre optic can be provided with sensing equipment suitable for sensing physiological signals of a specific organ of the host patient, such as the heart, vessels, brain, etc., or for characterizing concentrations of specific components, for example in blood. An emitted light beam or light pulse is aimed at a target tissue, and the light reflected from or transmitted through said target tissue is captured and characterized. A physiological change in the target tissue may yield a variation in a specific property of the reflected or transmitted light, such as light intensity, light scattering, and the like. The characterization of the reflected or transmitted light beam can be performed by a photodetector or sensor positioned at or adjacent to the distal end of the fibre optic. Generally, however, as illustrated in FIG. 3, such photodetector (5d) or sensor is housed in the IMD and the reflected or transmitted light is sent to said photodetector through the fibre optic. Depending on the electronics contained in the IMD, any variation in the reflected or transmitted light can be either analyzed in situ by a CPU for further actions, such as the instantaneous electric stimulation of the target tissue or of a related tissue, or the information may be stored in an internal memory, and retrieved later by an external communication equipment for monitoring the evolution of the target tissue, or for analysing ex situ the variations for further actions.

Both stimulation and information exchange can be guaranteed by a same IMD if several fibre optics (9), gathered in a sheath (9s) are coupled to the IMD, with a corresponding number of micro-optics components (if required) and of inner light sources (5L) and photodetectors (5d), all in quasi-perfect alignment with one another. In some applications, such as treatment of Parkinson disease, two separate sets of electrodes are required, one for the right and the other for the left brain hemisphere. In such cases, the IMD may comprise two separate optical units as described above, with two separate fibre optics reaching, one the right, the other the left brain hemisphere. Alternatively, the IMD may comprise a single optical unit, comprising either one or, preferably, two light sources (5L), with a single outer mating structure for connecting at least two fibre optics in alignment with two corresponding reference points; one fibre optic is positioned in the right brain hemisphere, and the other fibre optic is positioned in the left brain hemisphere.

When a fibre optic is coupled and fixed to an IMD according to the present invention, the fibre optic can be in alignment with the corresponding reference point of the inner or outer surface of the thin window, with a tolerance of less than 50 µm, preferably less than 10 µm. Similarly, the light element including one or more of an inner light source (5L) or photodetector (5d) or inner fibre-optic can be in alignment with said corresponding reference point of the inner or outer surface of the thin window with a tolerance of less than 30 µm, preferably less than 10 µm. The corresponding reference point is preferably a central point of a micro-optics component integral to the inner or outer surface of the thin window. One of the keys to the present invention is to form a thin window (4w) which is an integral part of the monolithic block unit, with no joint, and thus allowing both a total hermeticity and a great accuracy in the positioning thereof, and of any micro-optics component.

With such configuration, light transmission efficacies never attained to date with IMD's can be achieved. This is important for increasing the autonomy of the IMD by limiting the power losses. For rechargeable batteries, this allows the extension of the time intervals required between two charging operations of the small batteries contained in the IMD. For non-rechargeable batteries, this allows the prolongation of the use of an IMD before having to replace it. Recharging operations are cumbersome and of great inconvenience to the host patients. With a single hermetic joint (7) (which is macroscopic) between the optical unit and the housing, and with no feedthrough, the interior of the IMD is securely sealed from the outer environment of the host patient body, thus enhancing the longevity of the IMD, and ensuring the treatment efficacy as well as the safety of the host patient.

An implantable medical assembly as discussed supra can be produced by a process comprising the following steps:
- (a) Forming an optical unit (3) by:
  - (i) forming a monolithic block unit (4) and a light unit (5) as discussed supra;
  - (ii) rigidly mounting to the inner mating structure of the monolithic block unit the light unit such that the light element is in alignment with the corresponding reference point of the inner or outer surface of the thin window, to form the optical unit;
- (b) forming an IMD by enclosing components in the inner volume of a housing (2) formed by sealingly coupling a secondary element (2s) to a main housing element (2m) by means of a secondary joint (7s), wherein, either
  - (i) the optical unit is an integral part of either the main housing element (2m) or the secondary element (2s); or
  - (ii) the optical unit is not an integral part of any housing element (2m, 2s), and one of the main housing element and secondary element comprises an opening (20) and the optical unit is sealingly coupled to said opening by a hermetic joint (7), and
- (c) coupling the connector (9c) of a fibre optic (9) to the outer mating structure (4om) of the monolithic block unit (4).

The secondary joint (7s) and, optionally, the hermetic joint (7) are preferably achieved by brazing, by diffusion bonding, by eutectic bonding, by gluing (adhesive bonding with e.g., a ceramic cement), or by welding, e.g., laser welding, including direct welding or using intermediate metals including titanium or gold;

Clearly, the most critical step is the production of the monolithic block unit (4), which requires great accuracy. In one embodiment a monolithic block unit as defined in the present invention can be produced by 3D printing using a transparent ceramic material. Off the shelves 3-D printing technologies are now available for producing complex shape parts made of ceramic materials.

In an alternative embodiment a monolithic block unit can be produced by a process comprising the following steps:
  providing a 3D computer assisted design of the monolithic block unit;
  providing a basic block of a transparent ceramic material, which is transparent to wavelengths comprised between 300 and 2200 nm, and of dimensions suitable for forming the monolithic block unit by removal of excess material;

selectively treating with a laser the excess material to be removed from the basic block for forming the monolithic block unit such as to obtain a laser treated block, wherein the thus laser treated excess material is rendered more sensitive to an etching treatment than the non-treated material;

etching the laser treated block with a chemical composition such as to remove the laser treated excess material from the basic block and thus obtaining a monolithic block unit.

The IMD is completed by forming a housing (2) defining an inner volume separated from an outer environment, and enclosing an electronic circuit and source of power, such that the optical unit is sealingly coupled to the housing with the inner surface of the thin window facing the inner volume of the housing and the outer surface of the thin window facing the outer environment.

Excellent results can be obtained using etching kits available on the market, with micro-optics components (4L) integrally formed at a surface of the thin window. For example, a monolithic block unit illustrated in FIG. 3 was produced from a basic block of fused silica, with a thin window having a mean thickness in the area excluding the micro-optics components of about 450 μm and a diameter of about 3.2 mm. The thin window comprised integrated micro-optics components of diameters of 200 and 400 μm, respectively, and protruded from the surface of the thin window by a maximum height of 100 μm.

The present invention concerns an implantable medical device as discussed supra and as defined in the appended claims, yielding the following advantages:

(a) The level of alignment of the various components of the optical unit and fibre optic of the IMD of the present invention is more accurate than possible with state of the art IMD's, assembling various components by welding; it follows that the transfer of optical energy between the interior and exterior of the IMD is higher, thus allowing a lower power consumption and a longer autonomy of the battery located inside the housing.

(b) The number of external hermetic joints (7) exposed to the outer environment is substantially reduced, and a single hermetic joint suffices between the housing opening and the optical unit. In the absence of any feedthrough, this single hermetic joint, of macroscopic dimensions and easy to form ensures a tight contact between the optical unit and the housing. The optical unit, with the monolithic block unit, comprises no external joint, since the window is an integral part of the monolithic block unit.

(c) The use of a transparent ceramic material for the monolithic block unit ensures both a high light transmittance at the level of the thin window, and a low permeability to contaminants present in the outer environment of the IMD, when implanted in a host patient.

(d) The outer mating structure permits a surgeon to easily connect in situ a fibre optic to the IMD, with an accuracy of within 50 μm, preferably of within 10 μm, by simply inserting a connector into the outer mating structure. Fixing means, like screws, a bayonet, or snap fittings can be used to secure the fibre optic in place.

| # | Feature |
|---|---|
| 1 | Implantable medical device |
| 2 | Housing |
| 2h | Header (or terminal body) |
| 2L | Housing lid |
| 2m | Main housing element |
| 2o | Housing opening |
| 2s | Secondary (housing) element |
| 3 | Optical unit |
| 4 | Monolithic block unit |
| 4im | Inner mating structure |
| 4L | Micro-optics component |
| 4om | Outer mating structure |
| 4r | Corresponding reference point |
| 4w | Thin window |
| 5 | Light unit |
| 5d | Photodetector |
| 5L | Light source |
| 5p | Printed circuit board of light unit |
| 6 | Fixing means |
| 6p | Fixing plate |
| 6s | Fixing screw |
| 7 | Hermetic joint |
| 7s | Secondary joint |
| 9 | Fibre optic |
| 9c | Connector of fibre optic |
| 9e | Electrode |
| 9pv | Photovoltaic cell |
| 9s | Sheath of fibre optics bundle |

The invention claimed is:

1. An implantable medical device comprising:
   a. a housing defining an inner volume separated from an outer environment, and enclosing an electronic circuit and source of power, and
   b. an optical unit sealingly coupled to the housing, said optical unit comprising: a monolithic block unit made of a transparent ceramic material which is transparent to wavelengths comprised between 300 and 2200 nm, and comprising: a thin window defined by an inner surface facing the inner volume of the housing and an outer surface facing the outer environment, an outer mating structure located on the side of the outer surface of the thin window, for coupling an outer fibre optic in alignment with a corresponding reference point of the inner or outer surface of the thin window, and an inner mating structure located on the side of the inner surface of the thin window, for permanently coupling a light unit, and a light unit comprising a light element including one or more of an inner light source, and/or photodetector, and/or inner fibre optic, said light unit being rigidly mounted in the inner mating structure of the monolithic block unit, such that one of the inner light source, and/or photodetector, and/or inner fibre optic is in alignment with said corresponding reference point of the inner or outer surface of the thin window; and said implantable medical device lacking a feedthrough.

2. The implantable medical device according to claim 1, wherein the thin window comprises a portion facing the light element having a thickness of not more than 2000 pm, preferably not more than 1000 pm, more preferably of not more than 500 pm and wherein said portion preferably has a transmittance of at least 75% for wavelengths comprised between 300 and 2200 nm.

3. The implantable medical device according to claim 1, comprising a micro-optics component for modifying the properties of a light beam which is either emitted by the inner light source in the direction of the outer surface, or emitted by an external light source in the direction of the inner surface and of the photodetector or inner fibre optic.

4. The implantable medical device according to claim 3, wherein the micro-optics component is an integral part of the inner or outer surface of the thin window and/or is rigidly fixed to the light unit.

5. The implantable medical device according to claim 4, wherein the corresponding reference point is located on the micro-optics component which is integral to the inner or outer surface of the thin window.

6. The implantable medical device according to claim 3, wherein the micro-optics component is an integral part of the inner or outer surface of the thin window and/or is rigidly fixed to the inner light source.

7. The implantable medical device according to claim 1, wherein the housing is formed by at least a main housing element and a secondary element sealed to the main housing element by a secondary joint, and wherein:
 a. The optical unit is an integral part of either the main housing element or the secondary element, or
 b. The optical unit is sealingly coupled by a hermetic joint to an opening provided either in the main housing element or the secondary element, and wherein the hermetic joint and/or the secondary joint are formed by brazing, by diffusion bonding, by eutectic bonding, by gluing (adhesive bonding), or by welding including metallization of the surfaces to be welded followed either by direct welding or by using intermediate metals including titanium or gold.

8. The implantable medical device according to claim 1, wherein the light element is aligned with the corresponding reference point of the inner or outer surface of the thin window, with a tolerance of less than 30 pm.

9. The implantable medical device according to claim 1, wherein the transparent ceramic material forming the monolithic block unit is selected from: fused silica, borosilicate, spinel, sapphire, or yttrium oxide.

10. A kit-of-parts comprising:
 a. an implantable medical device according to claim 1, and
 b. a fibre optic, comprising a proximal end provided with a connector mating the outer mating structure of the monolithic block, such that when connected to said outer mating structure, the fibre optic is in alignment with the corresponding reference point of the inner or outer surface of the thin window, with a tolerance of less than 50 pm.

11. The kit-of-parts according to claim 10, wherein the proximal end of the fibre optic is provided with a micro-optics component for modifying the properties of a light beam which is either emitted by the inner light source towards the fibre optic, or transmitted from the fibre optic towards the photodetector or inner fibre optic.

12. The kit-of-parts according to claim 10, wherein the fibre optic comprises a distal end provided either with,
 (A) an electrodes unit, said electrodes unit comprising:
  a. a photovoltaic cell able to convert the light energy transported by the fibre optic into electrical current, and
  b. at least two electrodes electrically connected to the photovoltaic cell; or
 (B) A micro-optics device for aiming an emitted light beam towards a target tissue.

13. An implantable medical assembly comprising:
 a. an implantable medical device according to claim 1, and
 b. a fibre optic, comprising a proximal end provided with a connector mating and engaged in the outer mating structure of the monolithic block, wherein the fibre optic is in alignment with the corresponding reference point of the inner or outer surface of the thin window, with a tolerance of less than 50 pm, and, wherein the light element is in alignment with said corresponding reference point of the inner or outer surface of the thin window, with a tolerance of less than 30 pm.

14. An implantable medical device comprising:
 a. a housing defining an inner volume separated from an outer environment, and enclosing an electronic circuit and source of power, and
 b. an optical unit sealingly coupled to the housing, said optical unit comprising: a monolithic block unit made of a transparent ceramic material which is transparent to wavelengths comprised between 300 and 2200 nm, and comprising: a thin window defined by an inner surface facing the inner volume of the housing and an outer surface facing the outer environment, an outer mating structure located on the side of the outer surface of the thin window, for coupling an outer fibre optic in alignment with a corresponding reference point of the inner or outer surface of the thin window, and an inner mating structure located on the side of the inner surface of the thin window, for permanently coupling a light unit, and a light unit comprising a light element including one or more of an inner light source, and/or photodetector, and/or inner fibre optic, said light unit being rigidly mounted in the inner mating structure of the monolithic block unit, such that the light element is in alignment with said corresponding reference point of the inner or outer surface of the thin window, with a tolerance of less than 10 pm.

* * * * *